United States Patent [19]

Balkovec

[11] Patent Number: 5,310,726
[45] Date of Patent: May 10, 1994

[54] LIPOPEPTIDE COMPOUNDS

[75] Inventor: James M. Balkovec, N. Plainfield, N.J.

[73] Assignee: Merck & Co., Inc., Rahway, N.J.

[21] Appl. No.: 495,652

[22] Filed: Mar. 19, 1990

[51] Int. Cl.$^5$ .................. A61K 37/02; C07K 5/12; C07K 7/06

[52] U.S. Cl. .................. 514/11; 514/9; 530/317

[58] Field of Search .................. 530/317; 514/9, 11

[56] References Cited

U.S. PATENT DOCUMENTS

| | | | |
|---|---|---|---|
| 4,287,120 | 9/1981 | Abbott et al. | 530/317 |
| 4,288,549 | 9/1981 | Boeck et al. | 435/119 |
| 4,293,489 | 10/1981 | Debono | 530/317 |
| 4,320,053 | 3/1982 | Abbott et al. | 530/317 |
| 4,322,338 | 3/1982 | Abbott et al. | 530/317 |

FOREIGN PATENT DOCUMENTS

WO82/00587 3/1982 World Int. Prop. O. .

OTHER PUBLICATIONS

Satoi et al., J. Antibiotics 30, 303 (1977).
Roy et al., J. Antibiotics 40, 275 (1987).
Debono et al., J. Antibiotics 42, 389 (1989).

*Primary Examiner*—Merrell C. Cashion, Jr.
*Assistant Examiner*—S. G. Marshall
*Attorney, Agent, or Firm*—Richard C. Billups; Mark R. Daniel

[57] ABSTRACT

Antifungal and antiparasital lipopeptide compounds stable in aqueous media are described. Stability in aqueous media render lipopeptides more useful for compositions for therapeutic applications.

5 Claims, No Drawings

LIPOPEPTIDE COMPOUNDS

The present invention is directed to a compound having the formula:

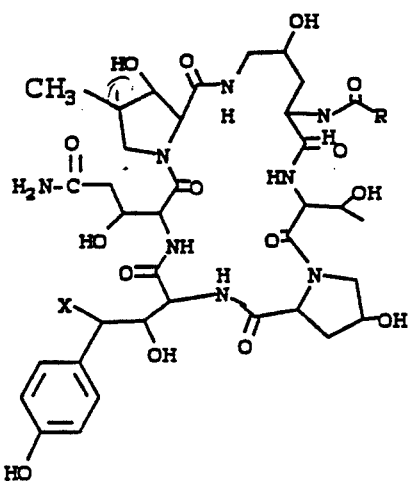

(I)

In this and succeeding formulas
X is hydrogen or hydroxyl, and
R is
a) a straight or branched chain alkyl from 5 to 23 carbon atoms;
b) a straight or branched chain alkenyl from 5 to 23 carbon atoms;
c) aryl, preferably phenyl and substituted phenyl wherein the substituent is selected from $C_1$ to $C_{10}$ alkyl, $C_1$ to $C_{10}$ alkoxy, $C_1$ to $C_{10}$ alkylamino or $C_1$ to $C_{10}$ thioalkoxy; and
d) heteroaryl, preferably pyrryl, thiophenyl, furyl, indolyl, benzothiophenyl, benzofuryl, imidazolyl, benzimidazolyl or pyridinyl Representative alkyls are normal and branched heptadecyl, heptyl, pentyl, nonadecyl, tridecyl, pentadecyl and the like.

Representative R groups when R is alkenyl are 8,11-heptadecadienyl, 2-pentenyl, 4-heptenyl, 7-pentadecenyl, 8-heptadecenyl, 10-heptadecenyl and the like.

Representative R groups when R is aryl and substituted aryl are phenyl, tolyl, xylyl, 2-ethylphenyl, 4-ethylphenyl, 4-isopropylphenyl, 4-isooctylphenyl, 4-tert-butylphenyl, 4-decylphenyl, 3-ethoxyphenyl, 4-isopropoxyphenyl, 4-(n-nonyloxy)phenyl, 4-(n-octyloxy)phenyl, 4-(n-decyloxy)phenyl, 2,4-dimethoxyphenyl, 4-(t-butoxy)phenyl, 2-methylthiophenyl, 4-(n-nonylthio)phenyl, 4-(n-octylthio)phenyl, mesityl and the like.

Representative R groups when R is heteroaryl are 2-pyrryl, 3-pyrryl, 2-furyl, 3-furyl, 2-pyridinyl, 3-pyridinyl, 4-pyridinyl, 2-indolyl, 2-benzofuryl, 2-benzimidazolyl, 2-imidazolyl, thiophene-2-yl, and the like.

The preferred compounds are those in which R is alkyl and alkenyl from 9 to 17 carbon atoms, substituted phenyl wherein the substituent is $C_4$ to $C_{10}$ alkyl, alkoxy, alkylamino or thioalkoxy.

An especially preferred compound is that in which X is H and R is 9,11-dimethyltridecyl and which may be represented by the formula:

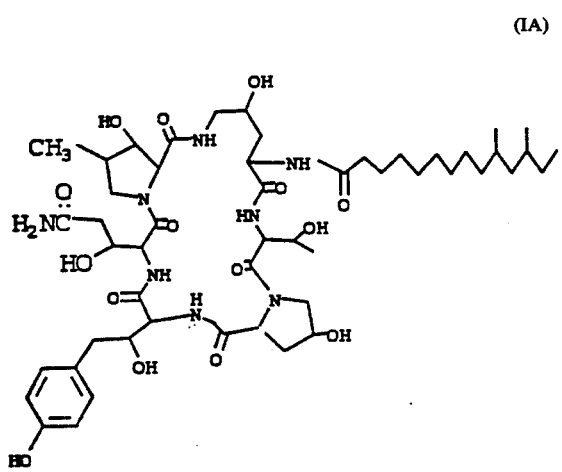

(IA)

The products of the present invention have been found to have antifungal and antiparasital activity as hereinafter detailed. Thus, they may be used against filamentous fungi such as *Cochlinbolus miyabeanus*, Aspergillus species, Penecillium species, Fusarium species, Alternaria species, Neurospora species and the like. They are especially useful for the treatment of mycotic infections, such as those caused by the *C. albicans*, *C. parapsilosis* and other Candida organisms, as well as for the prevention and or treatment of *Pneumocystis carinii* infections to which immune compromised patients are especially susceptible.

The compounds of the present invention are related to certain other lipopeptides which have been found to be useful for the control of organisms causing mycotic infections and for eradicating cysts formed in *Pneumocystis carinii* infections but which break down in aqueous media and therefore have limited usefulness. The compounds of the present invention, however, are stable in aqueous media, particularly in the physiological pH range. This property renders the compound more useful in compositions suitable for intravenous injections which is a preferred method of treatment.

The compounds are white or light colored solids which are soluble in many organic solvents such as methanol, ethanol, dimethylformamide, aqueous acetonitrile, pyridine, aqueous tetrahydrofuran, acetic acid and the like.

The compounds of the present invention may be obtained by intimately admixing Compound A, obtained as subsequently described, with a reducing agent and a strong acid according to the following equation.

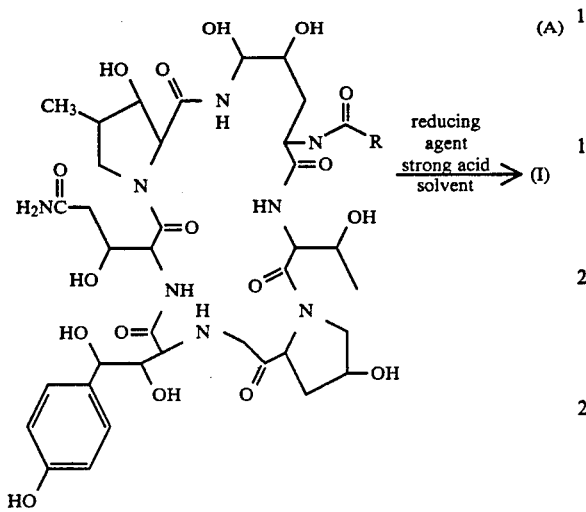

The reducing agents are selected from those which are stable in an acid environment. Representative of and particularly suitable are sodium cyanoborohydride, triethyl silicon hydride and sodium borohydride.

The reaction is carried out in the presence of a strong acid. Suitable strong acids include trifluoroacetic acid and trichloroacetic acid.

The product of the reduction may be a bis-reduced product or a mono-reduced product. When it is desired to obtain a mono-reduced product, namely, a product in which X is OH in formula (I) (Compound Ib), a solvent is employed. The solvent may be protic or non-protic. The preferred solvent for obtaining a mono-reduced product is glacial acetic acid.

When a bis-reduced product, X in formula (I) is H (Compound Ia) is desired, a separate solvent is not necessary. The strong acid serves as a suitable reaction medium.

The reaction may be summarized as follows:

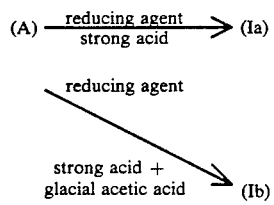

A by-product mono-reduction product (Ic) is also obtained, i.e., a compound which may be represented by the following formula:

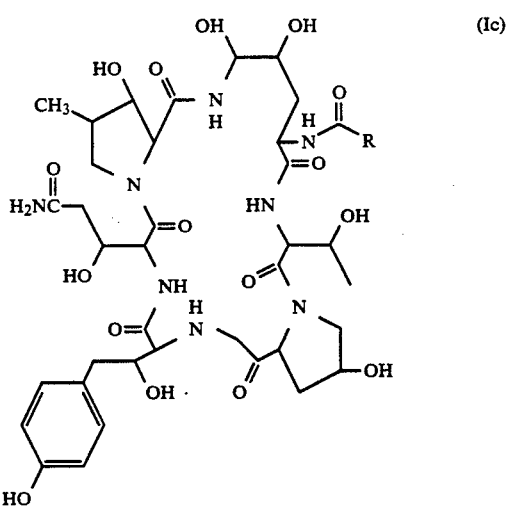

Compound Ic does not exhibit the stability in aqueous medium desired as do Compounds Ia and Ib, thus it is not within the scope of the present claims.

In carrying out the reaction to obtain Compound Ia, the lipopeptide is dissolved in the strong acid and to the resulting solution, is added the reducing agent while stirring at ambient temperature. Usually, the reaction takes place immediately, but stirring is continued for from about 0.5 to 4 hours to insure completion of the reaction and the formation of Compound Ia. At the end of this period, the volatiles are removed under reduced pressure to obtain a residue which is purified by reverse phase chromatography employing water/acetonitrile to obtain a purified product.

When the desired product is the mono-reduced product, essentially the same procedure is employed except that the reactant lipopeptide is first dissolved in glacial acetic acid. Thereafter, the acid is added followed by the reducing agent until the mono-reduced product is formed. This can be determined by a high performance liquid chromatography (HPLC) assay combined with an NMR determination. The product may be recovered and purified in the same manner as for the bis-reduced product.

The compounds of the present invention are useful as antifungal agents, both against filamentous fungi and yeasts, and they are also useful as antiparasital agents, especially against protozoal parasites. As antifungal agents, the compounds are especially useful against Candida species as hereinafter more fully illustrated, but they are also active against filamentous fungi such as *Aspergillus flavus*, *Aspergillus fumigatus*, *Aspergillus niger*, *Cochliobolus miyabeanus* and the like. As antiparasital or antiprotozoal agents, they may be useful for the control of organisms causing amebiasis such as *Entamoeba histolytica*, or organisms causing malaria such as Plasmodium species, or other organisms such as Trypanosoma species and the like. They are especially useful in inhibiting or alleviating *Pneumocystis carinii* infections. In such use Compound I or a composition containing Compound I is administered in a therapeutically effective or inhibitory amount to subjects infected with or susceptible to being infected with *Pneumocystis carinii*.

The efficacy of the compounds of the present invention for therapeutic or anti-infective purposes against

*Pneumocystis carinii* may be demonstrated in studies on immunosuppressed rats.

In a representative study, the effectiveness of Compound Ia was determined. Sprague-Dawley rats (weighing approximately 250 grams) were immunosuppressed with dexasone in the drinking water (2.0 mg/L) and maintained on a low-protein diet for five weeks to induce the development of pneumocystis pneumonia from a latent infection. Before drug treatment 2 rats were sacrificed to confirm the presence of *Pneumocystis carinii* pneumonia (PCP); both rats were found to have infections. Five rats (weighing approximately 150 grams) were injected intraperitoneally (IP) twice daily for four days with Compound Ia in 0.25 milliliters of 10% dimethylsulfoxide (DMSO) to supply drug at 0.6, 1.2 and 2.5 mg/kg of body weight. Control animals received 10% DMSO alone. All animals continued to receive dexasone in the drinking water and low protein diet during the treatment period. At the completion of the treatment, all animals were sacrificed, the lungs were removed and processed, and the extent of disease determined by microscopic analysis of stained slides. The results of the study showed that Compound Ia was effective in eliminating *P. carinii* cysts in four days with an $ED_{90}$ between 0.6 and 1.2 mg/kg.

The usefulness of the compounds as antifungal agents particularly, for the treatment of mycotic infections may be illustrated with minimum fungicidal concentration (MFC) results with Compound IA in tests against *Candida albicans*, *Candida tropicalis* and *Candida parapsilosis*.

The activity may be seen in a microdilution broth assay employing Yeast Nitrogen Base (Difco) with 10% dextrose (YNBD) as the medium. In carrying out the assay, Compound Ia was solubilized in 10 percent dimethyl sulfoxide (DMSO) and diluted to 2560 µg/ml. The compounds were then diluted to 256 µg/ml in YNBD. 0.15 ml of the suspension was dispensed to the top row of a 96-well plate (each well containing 0.15 ml of YNDB) resulting in a drug concentration of 128 µg/ml. Two-fold dilutions were then made from the top row to obtain final drug concentrations ranging from 128 to 0.06 µg/ml.

The yeast cultures, maintained on Sabouraud dextrose agar were transferred to YM broth (Difco) and incubated overnight at 35° C. with shaking (250 rpm). After incubation, each culture was diluted in sterile water to yield a final concentration of $1-5 \times 10^6$ colony forming units (CFU)/ml.

96-well microplates were inoculated using a MIC-2000 (Dynatech) which delivers 1.5 ml per well yielding a final inoculum per well of $1.5-7.5 \times 10^3$ cells. The microplates were incubated at 35° C. for 24 hours. The minimum inhibitory concentrations (MICS) were recorded as the lowest concentrations of drug showing no visible growth.

After recording the MIC, the plates were shaken to resuspend the cells. Thereafter, 1.5 ml samples from the wells in the 96-well microplate were transferred to a single well tray containing Sabouraud dextrose agar. The inoculated trays were incubated 24 hours at 28° C. and then read. The MFC is defined as the lowest concentration of drug showing no growth or less than 4 colonies per spot. The results were as follows:

| Fungi Strain No. | Minimum Fungicidal Concentration (µg/ml) |
|---|---|
| *Candida albicans* | |
| MY 1055 | 1 |
| MY 1585 | 0.25 |
| MY 1208 | 2 |
| MY 1028 | 0.5 |
| MY 1750 | 0.25 |
| MY 1783 | 0.5 |
| *Candida tropicalis* | |
| MY 1012 | 1 |
| *Candida parapsilosis* | |
| MY 1008 | 8 |
| MY 1010 | 4 |

Compound I has potential as a replacement for a known antifungal agent which while effective as an antifungal agent is of limited utility for having lytic effect on red blood cells. Red blood cell lysis, a harmful and potentially fatal side reaction is shown by many compounds at concentrations approaching the therapeutic dose and this property has limited the applicability of these compounds as drugs. The compound of the present invention would require a concentration far above the therapeutic dose before red blood cell lysis could occur.

The compounds of the present invention may be effectively utilized by formulating into various novel pharmaceutical compositions including tablets, capsules, aerosols, injectible compositions and oral liquid compositions. However, the outstanding stability of the compounds in aqueous media not possessed by the precursor compounds, render the compounds of the present invention particularly adaptable to use in formulating injectible compositions or oral liquid compositions.

For both antifungal and for antipneumocystis use, Compound I may be formulated for intravenous or intraperitonal injection. The compositions may be presented in unit dosage form in ampoules or in multidose containers if necessary with an added preservative. The compositions may also take such forms as suspensions, solutions or emulsions in oily or aqueous vehicles such as 0.85 percent sodium chloride or 5 percent dextrose in water, and may contain formulating agents such as suspending, stabilizing and/or dispersing agents. Buffering agents as well as additives such as saline or glucose may be added to make the solutions isotonic. The drug also may be solubilized in alcohol/propylene glycol or polyethylene glycol for drip intravenous administration. For topical applications, the drug may be formulated in conventional creams and ointments such as white petrolatum, anhydrous lanolin, cetyl alcohol, cold cream, glyceryl/monostearate and the like. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of one of the compounds.

When the compound is to be employed for control of pneumocystis infections it is desirable to directly treat lung and bronchi. For this reason, inhalation methods are preferred. For administration by inhalation, the compounds of the present invention are conveniently delivered in the form of an aerosol spray presentation from pressurized packs of nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of Compound I in suitable propellants, such as fluorocarbons or hydrocarbons.

The following examples illustrate the invention but are not to be construed as limiting:

EXAMPLE I

1-[4-hydroxy-$N^2$-(10,12-dimethyl-1-oxo-tetradecyl)ornithine]-4-[3-hydroxy-homotyrosine]-5-[3-hydroxy-glutamine]echinocandin B 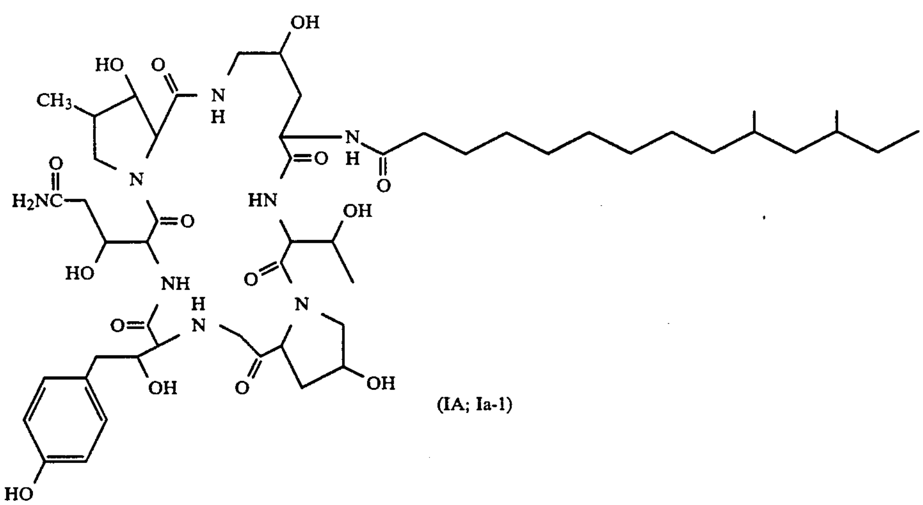 (IA; Ia-1)

1.02 grams (0.90 mmol) of 1-[4,5-dihydroxy-$N^2$-(10,12-dimethyl-1-oxotetradecyl)ornithine]-5-(3-hydroxy-glutamine)echinocandin B (compound of formula A when R is 9,11-dimethyltridecyl) was dissolved in 5 milliliters of trifluoroacetic acid and 307 milligrams (4.89 mmol) of sodium cyanoborohydride immediately added. The resultant solution was stirred at room temperature for 30 minutes. The mixture was then subjected to reduced pressure to remove the solvents and to recover a white solid residue. The latter was purified by reverse phase HPLC (2.12×25 cm C8 "Zorbax" column) using water/acetonitrile(45/55) at 10 mL/min and lyophilizing the appropriate eluate fractions as determined by NMR to obtain 410 milligrams (44 percent yield) of a white solid having the following spectral properties: 'H-NMR (300 MHz, $CD_3OD$): δ 7.02 (d, J=8 Hz, 2H), 3.76 (dd, J=15, 3 Hz, 1H), 2.99 (dd, J=15, 3 Hz, 1H).

Mass Spectrum (FAB): 1047 (M+1).

EXAMPLE II

1-[4-hydroxy-$N^2$-(10,12-dimethyl-1-oxo-tetradecyl)ornithine]-5-[3-hydroxy-glutamine]echinocandin B 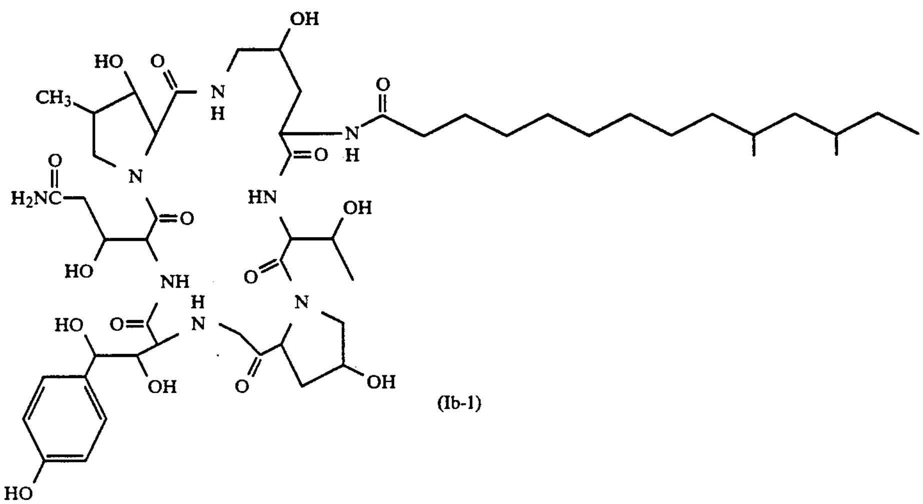 (Ib-1)

201.6 milligrams (0.19 mmol) of Compound A-1 (R=9,11-dimethyltridecyl) was dissolved in 5.0 milliliters of glacial acetic acid. To the resulting solution was added 2.0 milliliters (26 mmol) of trifluoroacetic acid followed by 124.6 mg (1.98 mmol) of sodium cyanoborohydride as a solid. After 105 minutes, the mixture was concentrated to obtain a solid. The solid was purified by preparative HPLC ("Zorbax" C8) using water/acetonitrile (45/55) as eluant to obtain several products: two monoreduced products and a bis reduced product.

The monoreduced products were stirred in methanol containing a trace of p-toluenesulfonic acid for several hours. At this time the mixture was concentrated and then purified by preparative HPLC and the eluates then concentrated and lyophilized to obtain the monoreduction product, Compound Ib (R=9,11-dimethyltridecyl).

'H-NMR (300 mHz, CD$_3$OD); δ 7.16 (d, J=9 Hz, 1H) and 6.77 (d, J=9 Hz, 1H), 3.73 (dd, J=9, 2 Hz, 1H), 2.98 (dd, J=9, 2 Hz, 1H).

Mass Spectrum (FAB): 1063 (M+1)

EXAMPLE III

In a manner similar to that described in Example I, the following compounds may be prepared:

TABLE I

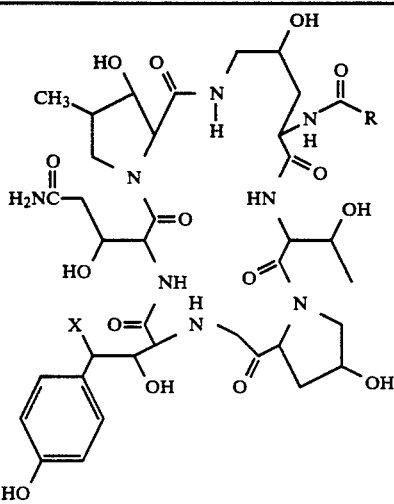

| | X | R | MW |
|---|---|---|---|
| (1) | H | —C$_{13}$H$_{27}$(n) | 1018 |
| (2) | H | —C$_{17}$H$_{25}$(n) | 1074 |
| (3) | H | —(CH$_2$)$_7$CH=CHCH$_2$CH=CH(CH$_2$)$_4$CH$_3$ | 1070 |
| (4) | H | —(CH$_2$)$_7$(CH=CHCH$_2$)$_3$CH$_3$ | 1068 |
| (5) | H | —(CH$_2$)$_7$C=C(CH$_2$)$_7$CH$_3$ | 1072 |
| (6) | H | —C$_6$H$_4$—O—C$_8$H$_{17}$ | 1040 |
| (7) | H | —C$_6$H$_4$—C$_9$H$_{19}$ | 1038 |
| (8) | H | —C$_6$H$_4$—NH—C$_4$H$_9$ | 983 |
| (9) | H | —C$_6$H$_4$—S—C$_{10}$H$_{21}$ | 1084 |
| (10) | OH | —C$_{15}$H$_{31}$(n) | 1062 |

TABLE I-continued

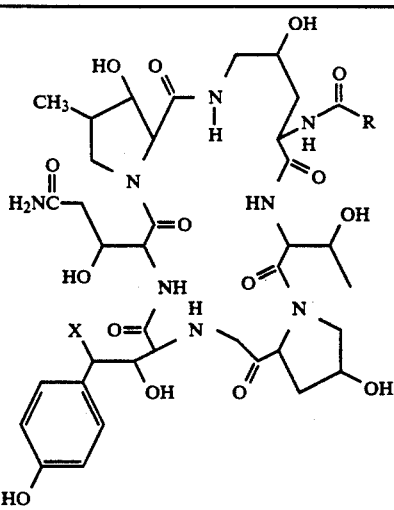

| | X | R | MW |
|---|---|---|---|
| (11) | OH | —(CH$_2$)$_8$—CH$_2$—CH$_2$—CHCH$_2$CH$_3$ (C$_2$H$_5$) | 1062 |
| (12) | OH | —C$_6$H$_4$—O—C$_8$H$_{17}$ | 1056 |

EXAMPLE IV 250 milliliters of an injectable preparation are prepared by conventional procedures having the following formulation:

| Dextrose | 12.5 grams |
|---|---|
| Water | 250 milliliters |
| Compound IA | 400 milligrams |

The ingredients are blended and thereafter sterilized for use.

EXAMPLE V

An injectable preparation is prepared by combining the following:

| | mg/ml |
|---|---|
| Compound Ib, R = 9,11-dimethyltridecyl | 10 |
| Methyl cellulose | 5.0 |
| Tween 80 | 0.5 |
| Benzyl alcohol | 9.0 |
| Benzalkonium chloride | 1.0 |
| Water to 1 ml | |

Starting Material

Compound A, (when R is 9,11-dimethyltridecyl) the starting material, may be obtained by cultivating *Zalerion arboricola* ATCC 20868, in a nutrient medium providing sources of carbon, nitrogen and inorganic salts, preferably in a medium having a polyol, for 7 to 14 days with or without agitation, then recovering the desired metabolite by adding methanol and preferably partitioning into an oxygenated solvent such as ethyl acetate, thereafter removing the solvent and dissolving the residue in a solvent suitable for one or more chromatographic separations as also described in copending application Ser. No. 362,647, filed Jun. 7, 1989 which is a continuation-in-part of Ser. No. 105,795, filed Oct. 9, 1987, now abandoned.

When Compound A is a compound in which R is other than 9,11-dimethyltridecyl, it may be prepared by deacylating the above natural product (Compound A) R=9,11-dimehyltridecyl with *Pseudomonas acidovorans* by adding a dimethyl sulfoxide solution thereof to a resting suspension of washed *Pseudomonas acidovorans* cells in phosphate buffer at pH 6.5 and incubating for 24 hours or longer in the temperature range of 20° to 60° C. and thereafter separate from the fermentation broth by conventional methods, centrifuging to separate the cells, loading the supernatant onto a chromatographic column, eluting with methanol and concentrating to obtain a deacylated cyclohexapeptide.

The deacylated cyclopeptide then may be acylated by intimately contacting the cyclohexapeptide with an active ester $$\underset{RCX}{\overset{O}{\|}}$$

where X is an appropriate leaving group such as chloride, pentafluorophenoxide, p-nitrophenoxide and the like in a solvent such as dimethylformamide, and intimately contacting for 16 to 20 hours at ambient temperature, then recovering the acylated compound with the appropriate R (Compound A where R is other than 9,11-dimethyltridecyl) by conventional procedures, such as concentrating, purifying the residue with preparative HPLC over a "Zorbax" (DuPont) C8 1-inch diameter column with acetonitrile/water, concentrating the appropriate fractions as determined by NMR and lyophilizing.

What is claimed is:

1. A compound having the formula:

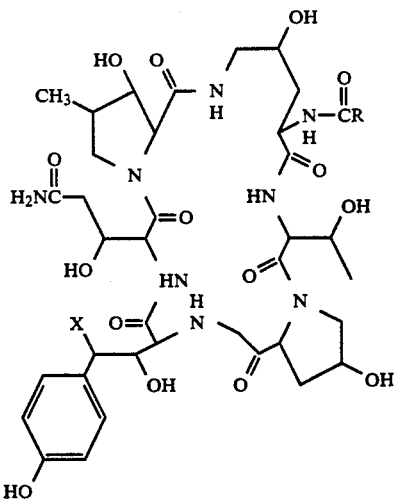

where
X is H or OH,
R is
 (a) a straight or branched chain alkyl from 5 to 23 carbon atoms,
 (b) a straight or branched chain alkenyl from 5 to 23 carbon atoms,
 (c) phenyl and substituted phenyl wherein the substituent is $C_1$ to $C_{10}$ alkyl, $C_1$ to $C_{10}$ alkoxy, $C_1$ or $C_{10}$ alkylamino, or $C_1$ to $C_{10}$ thioalkoxy; or
 (d) heteroaryl selected from the group consisting of pyrryl, thiophenyl, furyl, indolyl, benzothiophenyl, benzofuryl, imidazolyl, benzimidazolyl, and pyridinyl.

2. A compound according to claim 1 wherein X is H and R is 9,11-dimethyltridecyl.

3. A compound according to claim 1 wherein X is OH and R is 9,11-dimethyltridecyl.

4. A composition comprising a compound of claim 1 in intimate admixture with a pharmaceutically acceptable carrier.

5. A composition suitable for the treatment of mycotic or protozoal infections comprising a therapeutically effective amount of a compound of claim 1 in intimate admixture with an aqueous pharmaceutical carrier.

* * * * *